(12) United States Patent
Thrun et al.

(10) Patent No.: US 10,836,715 B2
(45) Date of Patent: Nov. 17, 2020

(54) PROCESS FOR PREPARING AN ORGANIC SULFONE

(71) Applicant: BASF SE, Ludwigshafen am Rhein (DE)

(72) Inventors: Frauke Thrun, Mannheim (DE); Joaquim Henrique Teles, Ludwigshafen am Rhein (DE); Jun Gao, Ludwigshafen am Rhein (DE)

(73) Assignee: BASF SE (DE)

( * ) Notice: Subject to any disclaimer, the term of this patent is extended or adjusted under 35 U.S.C. 154(b) by 0 days.

(21) Appl. No.: 16/314,720

(22) PCT Filed: Jul. 6, 2017

(86) PCT No.: PCT/EP2017/066857
§ 371 (c)(1),
(2) Date: Jan. 2, 2019

(87) PCT Pub. No.: WO2018/007481
PCT Pub. Date: Jan. 11, 2018

(65) Prior Publication Data
US 2019/0202778 A1    Jul. 4, 2019

(30) Foreign Application Priority Data
Jul. 8, 2016    (EP) .................................... 16178610

(51) Int. Cl.
*C07C 315/02*    (2006.01)

(52) U.S. Cl.
CPC ........... *C07C 315/02* (2013.01); *Y02P 20/582* (2015.11)

(58) Field of Classification Search
CPC ............................. C07C 315/02; Y02P 20/582
See application file for complete search history.

(56) References Cited

U.S. PATENT DOCUMENTS

| | | | |
|---|---|---|---|
| 4,097,526 A | 6/1978 | Chan | |
| 4,248,795 A | 2/1981 | Chan | |
| 4,395,363 A * | 7/1983 | Crawford | ............... C11D 1/755 510/340 |
| 9,969,708 B2 | 5/2018 | Vautravers et al. | |
| 10,087,395 B2 | 10/2018 | Pelzer et al. | |
| 10,112,882 B2 | 10/2018 | Thrun et al. | |
| 10,144,691 B2 | 12/2018 | Vautravers et al. | |
| 10,195,598 B2 | 2/2019 | Riedel et al. | |
| 10,202,324 B2 | 2/2019 | Vautravers et al. | |
| 2017/0137377 A1 | 5/2017 | Ueki et al. | |
| 2017/0246620 A1 | 8/2017 | Parvulescu et al. | |
| 2017/0275225 A1 | 9/2017 | Riedel et al. | |
| 2018/0208745 A1 | 7/2018 | Vautravers et al. | |
| 2018/0230117 A1 | 8/2018 | Teles et al. | |
| 2018/0290959 A1 | 10/2018 | Thrun et al. | |
| 2018/0312458 A1 | 11/2018 | Thrun et al. | |
| 2018/0346478 A1 | 12/2018 | Werner et al. | |
| 2018/0362351 A1 | 12/2018 | Parvulescu et al. | |
| 2018/0362353 A1 | 12/2018 | Vautravers et al. | |

FOREIGN PATENT DOCUMENTS

| | | |
|---|---|---|
| CN | 104557626 A | 4/2015 |
| JP | H01106858 A | 4/1989 |
| SU | 765262 A1 | 9/1980 |
| WO | WO-2008073694 A1 | 6/2008 |
| WO | WO-2015198850 A1 | 12/2015 |

OTHER PUBLICATIONS

U.S. Appl. No. 16/076,600, filed Aug. 8, 2018.
U.S. Appl. No. 16/307,450, filed Dec. 5, 2018.
U.S. Appl. No. 16/311,198, filed Dec. 19, 2018.
Database WPI, Week 198922, Thomson Scientific, London, GB, 1989, XP002765795, 2 pages.
European Search Report for EP Patent Application No. 16178610, dated Feb. 10, 2017.
Lakomova, N.A., et al., "4,4'-Dichlorodiphenyl sulfone", Database CAPLUS [Online], Chemical Abstracts Service, XP002774592, retrieved from STN Database accession No. 1981:174650, 1 page.
Yang, D., et al., "Process for preparing 4,4'-dichlorodiphenyl sulfone by sulfoxide oxidation method", Database CAPLUS [Online], Chemical Abstracts Service, XP002774593, retrieved from STN Database accession No. 2015:745488, 2 pages.
International Preliminary Examination Report for PCT/EP2017/066857 dated Jun. 29, 2018.
International Search Report for PCT/EP2017/066857 dated Oct. 23, 2017.
Written Opinion of the International Searching Authority for PCT/EP2017/066857 dated Oct. 23, 2017.

* cited by examiner

*Primary Examiner* — Rosalynd A Keys
(74) *Attorney, Agent, or Firm* — Faegre Drinker Biddle & Reath LLP

(57) ABSTRACT

A process for preparing polyaryl ethers in which a polycondensation of the monomer building blocks is carried out using microwave irradiation leads to thermoplastic molding compositions having improved color properties.

19 Claims, No Drawings

PROCESS FOR PREPARING AN ORGANIC SULFONE

CROSS-REFERENCE TO RELATED APPLICATIONS

This application is a national stage application (under 35 U.S.C. § 371) of PCT/EP2017/066857, filed Jul. 6, 2017, which claims benefit of European Application No. 16178610.8, filed Jul. 8, 2016, both of which are incorporated herein by reference in their entirety.

The present invention relates to a process for preparing an organic sulfone by oxidation of the respective organic sulfoxide.

Organic sulfones which are chemical compounds having a general structural formula $R^a$—$S(=O)_2$—$R^b$ where $R^a$ and $R^b$ are organic moieties widely used in chemical industry. For example, diaryl sulfones, such as 4,4'-dichlorodiphenylsulfone are important precursors for the production of polymers.

According to U.S. Pat. No. 4,097,526 A, an organic sulfone is prepared in an in-situ process by oxidizing the corresponding sulfide with a mixture of hydrogen peroxide and a carboxylic acid in the presence of a catalytic amount of a mineral acid or an organic sulfonic acid.

WO 2015/198850 A1 discloses the oxidation of 4-(trifluoromethyl sulfinyl) phenol with hydrogen peroxide in the presence of at least one acid selected from a group I consisting of sulfuric acid and a $C_1$ to $C_6$ alkansulfonic acid, which may be substituted with a halogen and at least one compound, selected from a group II consisting of $C_2$ to $C_{12}$ aliphatic carboxylic acids and sulfolane.

JP H01-106 858 discloses hydrogen peroxide, hypochlorite or nitric acid as oxidizing agents for halogen-substituted diphenyl sulfide into the respective sulfone. Sulfoxide is mentioned as an intermediate of the reaction. The use of hydrogen peroxide in the presence of glacial acetic acid, a mixture of acetic acid and acetic anhydride or bicarbonate is disclosed.

The present disclosure relates to a process for the manufacture of an organic sulfone via oxidation of the corresponding sulfoxide, which makes efficient use of the educt. The present disclosure further relates to such a process, which gives high overall product yields. Moreover, it relates to such a process, which is simple and cost efficient. In particular, the present disclosure relates to such a process, which has an overall good energy efficiency.

Hereunder, a process is disclosed for the preparation of an organic sulfone by oxidation of the respective sulfoxide the presence of at least one peroxide, which comprises at least one carboxylic acid, which is liquid at 40° C. and has a miscibility gap with water at 40° C. and atmospheric pressure.

In addition, this disclosure pertains to the use of the sulfone obtained from 4,4'-dichlorodiphenylsulfoxide by said process for the manufacture of polymers comprising sulfone groups. It further pertains to a fiber, film or shaped article produced from a polymer obtained from 4,4'-dichlorophenylsulfoxide.

With the process disclosed herein an organic sulfone is prepared by oxidation from the respective sulfoxide. The organic sulfone is not particularly limited. The organic sulfone may have the general formula given above and may have one or more, such as two or three, —$SO_2$— entities in the molecule. It may be preferred that the organic sulfone has only one —$SO_2$— entity in the molecule.

A process as disclosed herein may particularly be preferred wherein the sulfone has a structure of formula (I)

(I)

wherein R1 and R2 are independently from each other
  substituted or unsubstituted $C_6$ or $C_{10}$ aryl, wherein the substituents are halogen, hydroxy, cyano, nitro, linear or branched $C_1$ to $C_5$ alkyl, or linear or branched $C_1$ to $C_5$ alkoxy,
  linear or branched, substituted or unsubstituted $C_1$ to $C_{20}$ alkyl, wherein the substituents are halogen, tertiary hydroxy, cyano, nitro, carboxy, substituted or unsubstituted $C_6$ to $C_{10}$ aryl, $C_2$ to $C_{10}$ alkenyl, linear or branched $C_1$ to $C_5$ alkoxy, $C_5$ to $C_7$ cycloalkyl or $C_5$ to $C_7$ cycloalkenyl,
  linear or branched, substituted or unsubstituted $C_3$ to $C_{20}$ alkenyl, wherein the substituents are halogen, tertiary hydroxy, cyano, nitro, $C_1$ to $C_5$ alkoxy or linear or branched $C_1$ to $C_{10}$ alkyl.

The organic sulfone has a melting point of at least 40° C. It may be most preferred that the sulfone has a melting point of at least 70° C., for instance at least 100° C., such as at least 120 to 200° C., such as 130° C., 140° C. or 150° C. In most cases, the sulfone has a melting point of not more than 220° C., even though the melting point of the sulfone may be higher e.g. up to 250° C. or even more.

It may be preferred that the sulfone has a structure of formula (I) wherein R1 and R2 are both a substituted or unsubstituted $C_6$ or $C_{10}$ aryl, wherein the substituents are halogen, hydroxy, cyano, nitro, linear or branched $C_1$ to $C_5$ alkyl, or linear or branched $C_1$ to $C_5$ alkoxy. It may be more preferred that R1 and R2 are both a substituted or unsubstituted $C_6$ aryl, wherein the substituents are halogen, hydroxy, cyano, nitro, linear or branched $C_1$ to $C_5$ alkyl, or linear or branched $C_1$ to $C_5$ alkoxy.

An example of a most preferred sulfone is 4,4'-dichlorodiphenylsulfone having a structure of formula (II)

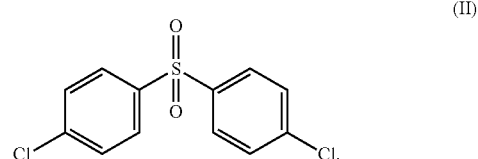 [SMILES: O=S(=O)(c1ccc(Cl)cc1)c1ccc(Cl)cc1]

(II)

With the process disclosed herein the organic sulfone is prepared from the respective sulfoxide. Therefore, the sulfoxide is an organic sulfoxide and has the structure of the organic sulfone with a —SO— entity instead of a —$SO_2$— entity of the product. The person skilled in the art understands that in case the product has more than one —$SO_2$— group, the respective educt respectively has more than one —SO— group.

Generally, it may be preferred to use a sulfoxide which is at least partially soluble in the at least one carboxylic acid, which is employed in the process disclosed herein. Thus, it may be preferred that the sulfoxide is at least partially soluble at 80° C. in the at least one carboxylic acid. It may particularly preferred that the sulfoxide has a solubility in the at least one carboxylic acid of at least 20 g/l at 80° C., and it may be more preferred that it has a solubility of at least 50 g/l at 80° C. and especially preferred a solubility of at least 100 g/l at 80° C. For example, the solubility may range of from 150 to 300 g/l at 80° C. The solubility is determined according to IUPAC, Compendium of Chemical Terminology, $2^{nd}$ ed. "Gold Book", Version 2.3.3, 2014-02-24, page 1397. It may be preferred that the sulfoxide is at least partially soluble in a temperature range of from 10 to 40° C. in the at least one carboxylic acid. It may particularly be preferred that the sulfoxide has a solubility in the at least one carboxylic acid of at least 5 g/l at 40° C., more preferred at least 10 g/l at 40° C. and especially preferred a solubility of at least 20 g/l at 40° C.

The sulfoxide may have one or more, such as two or three, —SO— entities in the molecule. It may be preferred to use an organic sulfoxide, which has only one —SO— entity in the molecule.

It may be particularly preferred to use a sulfoxide having a structure of formula (III)

wherein R1 and R2 are independently from each other
  substituted or unsubstituted $C_6$ or $C_{10}$ aryl, wherein the substituents are halogen, hydroxy, cyano, nitro, linear or branched $C_1$ to $C_5$ alkyl, or linear or branched $C_1$ to $C_5$ alkoxy,
  linear or branched, substituted or unsubstituted $C_1$ to $C_{20}$ alkyl, wherein the substituents are halogen, tertiary hydroxy, cyano, nitro, carboxy, substituted or unsubstituted $C_6$ to $C_{10}$ aryl, $C_2$ to $C_{10}$ alkenyl, linear or branched $C_1$ to $C_5$ alkoxy, $C_5$ to $C_7$ cycloalkyl or $C_5$ to $C_7$ cycloalkenyl,
  linear or branched, substituted or unsubstituted $C_3$ to $C_{20}$ alkenyl, wherein the substituents are halogen, tertiary hydroxy, cyano, nitro, $C_1$ to $C_5$ alkoxy or linear or branched $C_1$ to $C_{10}$ alkyl.

It may be preferred that the sulfoxide has a structure according to formula (III) wherein R1 and R2 are both a substituted or unsubstituted $C_6$ or $C_{10}$ aryl, wherein the substituents are halogen, hydroxy, cyano, nitro, linear or branched $C_1$ to $C_5$ alkyl, or linear or branched $C_1$ to $C_5$ alkoxy. It may be more preferred that R1 and R2 are both a substituted or unsubstituted $C_6$ aryl, wherein the substituents are halogen, hydroxy, cyano, nitro, linear or branched $C_1$ to $C_5$ alkyl, or linear or branched $C_1$ to $C_5$ alkoxy. It may be most preferred that the sulfoxide has a structure according formula (III) wherein R1 and R2 are both 4-chlorophenyl.

Generally, the choice of R1 and R2 in the sulfoxide is guided by the physical properties desired for the sulfone, in particular the melting point of the sulfone and the solubility of the sulfone in the at least one carboxylic acid.

According to the process disclosed herein, at least one peroxide is present, for example one or a mixture of two or more, such as three or more peroxides. Generally, the at least one peroxide may be added or it may be generated in situ. It may also be possible that the at least one peroxide is added and is generated in situ. If the at least one peroxide is added, it may be added as aqueous solution. The concentration thereof may for instance be of from 1 to 90% by weight, based on the solution. It may be preferred that the concentration is of from 30 to 70% by weight, based on the solution. In case the peroxide is generated in situ, the concentration thereof may be small or very small since it may be consumed instantaneously. Thus, it may be less than 0.1% by weight, based on the sulfoxide. The concentration of the at least one peracid generated in situ may however for instance also range of from 0.1 to 10% by weight or higher for instance up to 15% by weight, based on the sulfoxide.

Generally, the amount of the at least one peroxide depends on the amount of —SO— entities in the respective educt to be oxidized to the —$SO_2$— entities in the product. The amount of the at least one peroxide may range of from 1 to 2 equiv. based on sulfoxide. Thereby it may be preferred that the amount of the at least one peroxide ranges of from 1 to 1.5 equiv. based on sulfoxide.

The at least one peroxide may be at least one peracid, for example one or a mixture of two or more, such as three or more peracids. It may be preferred that the process disclosed herein is carried out in the presence of one or two peracids. The at least one peracid may be a $C_1$ to $C_{10}$ peracid, which may be unsubstituted or substituted, e.g. by linear or branched $C_1$ to $C_5$ alkyl or halogen, such as fluor. Examples thereof are peracetic acid, performic acid, perpropionic acid, percaprionic acid, pervaleric acid or pertrifluoroacetic acid. It may be particularly preferred that the at least one peracid is a $C_6$ to $C_{10}$ peracid. It may be preferred that the at least one peracid is one peracid. It may be most preferred that the peracid is 2-ethylhexanoic peracid. It may be advantageous that the at least one peracid which is soluble in water is added as aqueous solution. Further it may be advantageous that the at least one peracid which is not sufficiently soluble in water is added, in particular dissolved in the respective carboxylic acid. It may be most preferred that the at least one peracid is a $C_6$ to $C_{10}$ peracid, in particular a 2-ethylhexanoic peracid which is generated in situ.

It may be preferred that the at least one peroxide is $H_2O_2$. In particular, it may be that the $H_2O_2$ is added. It may be more preferred that the $H_2O_2$ is added as an aqueous solution, for instance of 1 to 90% by weight, such as a 20, 30, 40, 50, 60 or 70% by weight, based on the aqueous solution. It may be most preferred that it is a 30 to 70% by weight, such as 50 to 70% by weight, such as a 50% by weight solution, the % by weight being based on the aqueous solution. It may be particularly preferred that the $H_2O_2$ is added as an aqueous solution of 50 to 70% by weight, such as 60 or 70% by weight, whereby 70% by weight may be most preferred, the % by weight being based on the aqueous solution. Using highly concentrated aqueous solution of $H_2O_2$ may lead to a reduction of reaction time. It may also facilitate recycling the at least one carboxylic acid.

Generally, the amount of $H_2O_2$ depends on the amount of —SO— entities in the respective educt to be oxidized to the —$SO_2$— entities in the product. The amount of $H_2O_2$ may range of from 1 to 3 equivalents based on the used amount of sulfoxide. Thereby, it may be preferred that the amount of $H_2O_2$ ranges of from 1.0 to 2.5 equivalents based on the used amount of sulfoxide. The amount of $H_2O_2$ may for instance range of from 1 to 2 equiv. based on sulfoxide. Thereby it may be preferred that the amount of $H_2O_2$ ranges of from 1 to 1.5 equiv. based on sulfoxide.

The at least one peroxide may be prepared by any suitable method. Such methods are either known to the person skilled in the art or are accessible to him by application of his general knowledge.

The process disclosed herein comprises at least one carboxylic acid, that is to say one or a mixture of two or more, such as three or more carboxylic acids. It may be most preferred that it is one carboxylic acid. Said at least one carboxylic acid is a liquid at 40° C. That is to say that if the process disclosed herein is carried out comprising more than one carboxylic acid each carboxylic acid may be liquid at 40° C. It may also be possible that one or more carboxylic acids, which are solids at 40° C. dissolve in one or more carboxylic acids which are liquid at 40° C. It may be most preferred that in case more than one carboxylic acid is employed, all carboxylic acids are liquid at 40° C. To allow process measures to be carried out at low temperatures, it may be advantageous that the more than one carboxylic acid stays liquid below 40° C., such as of from 10 to 40° C. Generally, the liquid may have a dynamic viscosity of from 0.5 to 40 mPa*s at 20° C., preferred of from 1 to 15 mPa*s, measured in a cone and plate rotational viscometer according to DIN 53018 Part 1, March 1976.

As described above, it may be preferred that the at least one carboxylic acid is at least partially a solvent for the sulfoxide at 40° C. Further, it may be advantageous that the organic sulfone is at least partially soluble in the at least one carboxylic acid at 40° C. or higher, e.g. 50° C., 60° C. or 70° C. or higher.

Moreover, it may be most preferred that the organic sulfone is poorly or essentially not, in particular not soluble in the at least one carboxylic acid at 40° C. or below such as at a temperature of from 10 to 40° C. It may be very preferred that the organic sulfone has a solubility in the at least one carboxylic acid at 25° C. of 5% by weight or less, such as 4% by weight or less or 3% by weight or less, based on sulfone in the carboxylic acid and, determined according to GC analysis. Poor solubility of the organic sulfone may reduce product losses.

The at least one carboxylic acid has a miscibility gap with water at 40° C. and at atmospheric pressure. Thereby it may be preferred that if the process disclosed herein is carried out comprising more than one carboxylic acid, each carboxylic acid has a miscibility gap with water at 40° C. and at atmospheric pressure. The miscibility gap can be represented by a phase diagram, in which the composition of a mixture of two different liquids is plotted against the temperature. Connecting the points gives the bimodal curve. The bimodal curve encloses the area in which two liquids build out two phases, thus these phases are separated. Outside the bimodal curve the liquids are miscible, thus form a homogeneous mixture. IUPAC, Compendium of Chemical Terminology, $2^{nd}$ ed. "Gold Book", Version 2.3.3, 2014-02-24, page 937. At 40° C. and at atmospheric pressure, a concentration range exists where mixtures of water and carboxylic acid spontaneously separate into two separate liquid phases.

It may be preferred that the process disclosed herein comprises that water has—at atmospheric pressure—a solubility in the at least one carboxylic acid of less than 2% by weight, based on the water/carboxylic acid solution at 40° C., more preferred less than 1% by weight, based on the water/carboxylic acid solution, in particular less than 0.5% by weight, based on the water/carboxylic acid solution. It may be most preferred that water is not or essentially not soluble in the at least one carboxylic acid at 40° C. and atmospheric pressure. Generally, the solubility can be determined according to DIN 51777. Thereby it may be preferred that water—if the process disclosed herein is carried out comprising more than one carboxylic acid—has a solubility given above in each carboxylic acid.

Given the above proviso regarding the liquid state and the miscibility gap, the at least one carboxylic acid is not particularly limited. Thus, it may be a monocarboxylic acid. It may also be a mixture of one or more such as two or three or four monocarboxylic acids. It may be preferred that the at least one carboxylic acid is one or more such as two or three monocarboxylic acids. It may be most preferred that it is one monocarboxylic acid.

The at least one carboxylic acid may be at least one aliphatic carboxylic acid, whereby the at least one aliphatic carboxylic acid may be at least one linear or at least one branched aliphatic carboxylic acid or it may be a mixture of one or more linear and one or more branched aliphatic carboxylic acids. It may be preferred that the at least one carboxylic acid is at least one branched aliphatic carboxylic acid.

It may be preferred that the at least one carboxylic acid is an aliphatic $C_6$ to $C_{10}$ carboxylic acid, such as a $C_6$ to $C_9$ carboxylic acid. It may be more preferred that the at least one carboxylic acid is an aliphatic $C_7$ to $C_9$ carboxylic acid, whereby it may be even more preferred that the at least one carboxylic acid is an aliphatic monocarboxylic acid. Thus, the at least one carboxylic acid may be hexanoic acid, heptanoic acid, octanoic acid, nonanoic acid or decanoic acid or a mixture of one or more of said acids. For instance the at least one carboxylic acid may be n-hexanoic acid, 2-methyl-pentanoic acid, 3-methyl-pentanoic acid, 4-methyl-pentanoic acid, n-heptanoic acid, 2-methyl hexanoic acid, 3-methyl-hexanoic acid, 4-methyl-hexanoic acid, 5-methyl-hexanoic acid, 2-ethyl-pentanoic acid, 3-ethyl-pentanoic acid, n-octanoic acid, 2-methyl-heptanoic acid, 3-methyl-heptanoic acid, 4-methyl-heptanoic acid, 5-methyl-heptanoic acid, 6-methyl-heptanoic acid, 2-ethyl-hexanoic acid, 4-ethyl-hexanoic acid, 2-propyl pentanoic acid, 2,5-dimethylhexanoic acid, 5,5-dimethylhexanoic acid, n-nonanoic acid, 2-ethyl-heptanoic acid, n-decanoic acid, 2-ethyl octanoic acid, 3-ethyl-octanoic acid, 4-ethyl octanoic acid. It may also be a mixture of different structural isomers of one of said acids. For instance, the at least one carboxylic acid may be isononanoic acid comprising a mixture of 3,5,5-trimethylhexanoic acid, 2,5,5-trimethyl-hexanoic acid and 7-methyloctanoic acid or neodecanoic acid comprising a mixture of 7,7-dimethyloctanoic acid, 2,2,3,5-tetramethylhexanoic acid, 2,4-dimethyl-2-isopropylpentanoic acid and 2,5-dimethyl-2-ethylhexanoic acid. It may be most preferred that the at least one carboxylic acid is 2-ethylhexanoic acid or isononanoic acid.

The amount of the at least one carboxylic acid is not particularly limited. The person skilled in the art will appreciate that a large amount may be economically unprofitable. The person skilled in the art will likewise consider that if a very small amount is employed, the at least one carboxylic acid may not sufficiently support the oxidation or may not sufficiently act as solvent or both. Generally, it may be advantageous that the concentration of the sulfoxide in the solvent ranges from 10 to 30% by weight, based on the sulfoxide/carboxylic acid mixture. It may be more preferred that the concentration of the sulfoxide in the solvent ranges from 15 to 25% by weight, based on the sulfoxide/carboxylic acid mixture. It may be most preferred that the concentration of the sulfoxide in the solvent ranges from 15 to 20% by weight, based on the sulfoxide/carboxylic acid mixture.

While it may be possible to employ another solvent or a mixture of other solvents in addition to the at least one carboxylic acid, it is generally preferred that the at least one carboxylic acid is the sole solvent used in the process disclosed herein. If another solvent or a mixture of other solvents is used in addition to the at least one carboxylic acid, the amount of the additional solvent or solvent mixture is generally much lower than that of the at least one carboxylic acid and typically does not exceed more than 50% by weight, more preferably less than 30%, such as less than 20% by weight or less than 10% by weight or for instance 10 to 30% by weight, the weight being based on the weight of that at least one carboxylic acid and the other solvent or mixture of other solvents. The other solvent or mixture of other solvents may for instance be an azeotrope former with water such as monochlorobenzene or toluene.

The process disclosed herein may comprise the presence of at least one, such as one or more, such a mixture of two or three, additional acids. Said at least one additional acid may be an inorganic or organic acid. It may be preferred the at least one additional acid is at least one inorganic acid. Generally, it may be preferred that the at least one additional acid is at least one strong acid. It may be preferred that the at least one strong acid has a $pK_a$ value of from −9 to 3, for instance −7 to 3 in water. The person skilled in the art appreciates that such acid dissociation constant values, $K_a$, can be for instance found in a compilation such as in IUPAC, Compendium of Chemical Terminology, $2^{nd}$ ed. "Gold Book", Version 2.3.3, 2014-02-24, page 23. The person skilled in the art appreciates that such $pK_a$ values relates to the negative logarithm value of the $K_a$ value. It may be more preferred that the at least one strong acid has a negative $pK_a$ value, such as of from −9 to −1 or −7 to −1 in water. Examples of the at least one strong inorganic acid are nitric acid, hydrochloric acid, hydrobromic acid, perchloric acid, and/or sulfuric acid. It may be most preferred to use one strong inorganic acid, in particular, sulfuric acid. While it may be possible to use the at least one strong inorganic acid as aqueous solution, it may be preferred that the at least one inorganic acid is used neat. Examples of at least one strong organic acids are organic sulfonic acids, whereby it is possible that at least one aliphatic or at least one aromatic sulfonic acid or a mixture thereof is used. Para-toluenesulfonic acid, methanesulfonic acid or trifluormethanesulfonic acid are examples for the at least one strong organic acid. It may be most preferred to use one strong organic acid, in particular methanesulfonic acid.

It may be preferred that the at least one further acid, in particular the at least one strong acid is used in catalytic amounts. Thus, it may be advantageous that it is employed in amounts of from 10 to 30 mol %, more preferred of from 15 to 25 mol %, based on sulfoxide. It may be even more preferred to employ it in amount of less than 10 mol %, based on sulfoxide, such as in amounts of from 0.1 to 8 mol %, based on sulfoxide for example of from 0.1 to 3 mol %, based on sulfoxide. It may be particularly preferred to employ it in amounts of from 0.5 to 1 mol %, based on sulfoxide.

For example, the process disclosed herein may preferably be used for the preparation of organic sulfones from the sulfoxides in the presence of the peroxides and carboxylic acids listed below in Table 1:

| | Organic sulfone having a structure of formula I | Peroxide used (% by weight) | Amount (equiv based on sulfoxide) | Carboxylic acid used | Concentration sulfoxide in solvent[a] (weight-%) | Additional Acid used | Amount (equiv based on sulfide/sulfoxide) |
|---|---|---|---|---|---|---|---|
| 1.1 | R1 = R2 = phenyl-X; X = halogen, H, $C_1$-$C_5$ alkyl, $C_1$-$C_5$ alkoxy, OH | $H_2O_2$ (30-70%) | 1.0-1.2 | $C_7$-$C_{10}$[a] | 10-25 | Sulfonic/sulfuric acid[b] | 0.15-0.25 |
| 1.2 | R1 = R2 = phenyl-X; X = halogen, H, $C_1$-$C_5$ alkyl, $C_1$-$C_5$ alkoxy, OH | $H_2O_2$ (30-70%) | 1.0-1.2 | $C_7$-$C_{10}$[a] | 10-25 | Sulfonic/sulfuric acid[b] | 0.001-0.25 |
| 1.3 | R1 = R2 = phenyl-X; X = halogen, H, $C_1$-$C_5$ alkyl, $C_1$-$C_5$ alkoxy, OH | $H_2O_2$ (70%) | 1.0-1.5 | $C_7$-$C_{10}$[a] | 10-25 | Sulfonic/sulfuric acid[b] | 0.15-0.25 |

-continued

| Organic sulfone having a structure of formula I | Peroxide used (% by weight) | Amount (equiv based on sulfoxide) | Carboxylic acid used | Concentration sulfoxide in solvent[a] (weight-%) | Additional Acid used | Amount (equiv based on sulfide/ sulfoxide) |
|---|---|---|---|---|---|---|
| 1.4 R1 = R2 = (phenyl-X); X = halogen, H, $C_1$-$C_5$ alkyl, $C_1$-$C_5$ alkoxy, OH | $H_2O_2$ (70%) | 1.0-1.2 | $C_7$-$C_{10}$[a] | 15-25 | Sulfonic/ sulfuric acid[b] | 0.001-0.1 |
| 1.5 R1 = R2 = (4-Cl-phenyl) | $H_2O_2$ (30-70%) | 1.0-1.2 | 2-ethylhexanoic acid | 10-25 | $H_2SO_4$ | 0.15-0.25 |
| 1.6 R1 = R2 = (4-Cl-phenyl) | $H_2O_2$ (50%) | 1.0-1.2 | 2-ethylhexanoic acid | 15-20 | $H_2SO_4$ | 0.20 |
| 1.7 R1 = R2 = (4-Cl-phenyl) | $H_2O_2$ (50%) | 1.0-1.2 | 2-ethylhexanoic acid | 10-25 | $H_2SO_4$ | 0.1-0.3 |
| 1.8 R1 = R2 = (4-Cl-phenyl) | $H_2O_2$ (50%) | 1.0-2.0 | 2-ethylhexanoic acid | 15-20 | MSA | 0.20 |
| 1.9 R1 = R2 = (phenyl-X) | $H_2O_2$ (70%) | 1.0-2.0 | 2-ethylhexanoic acid | 15-20 | $H_2SO_4$ | 0.001-0.05 |
| 1.10 R1 = R2 = (4-Cl-phenyl) | $H_2O_2$ (30-70%) | 1.0-1.2 | 2-ethylhexanoic acid | 15-25 | MSA[c] | 0.15-0.25 |
| 1.11 R1 = R2 = (4-Cl-phenyl) | $H_2O_2$ (50%) | 1.0-1.2 | 2-ethylhexanoic acid | 15-20 | MSA | 0.20 |
| 1.12 R1 = R2 = (4-Cl-phenyl) | $H_2O_2$ (30-70%) | 1.0-1.2 | Isononanoic acid | 15-20 | $H_2SO_4$ | 0.15-0.25 |

-continued

| | Organic sulfone having a structure of formula I | Peroxide used (% by weight) | Amount (equiv based on sulfoxide) | Carboxylic acid used | Concentration sulfoxide in solvent[a] (weight-%) | Additional Acid used | Amount (equiv based on sulfide/ sulfoxide) |
|---|---|---|---|---|---|---|---|
| 1.13 | R1 = R2 = benzyl-C6H4-X | $H_2O_2$ (50%) | 1.0-1.2 | Isononanoic acid | 15-20 | $H_2SO_4$ | 0.20 |
| 1.14 | R1 = R2 = benzyl | $H_2O_2$ (70%) | 1.0-1.5 | Isononanoic acid | 10-25 | $H_2SO_4$ | 0.001-0.1 |
| 1.15 | R1 = benzyl-C6H4-X; X = halogen, H, $C_1$-$C_5$ alkyl, $C_1$-$C_5$ alkoxy, OH; R2 = $C_1$-$C_5$ alkyl, aryl | $H_2O_2$ (30-70%) | 1.0-1.2 | $C_7$-$C_{10}$[a] | 10-25 | Sulfonic/ sulfuric acid[b] | 0.15-0.25 |
| 1.16 | R1 = benzyl | $H_2O_2$ (30-70%) | 1.0-1.2 | 2-ethylhexanoic acid | 15-25 | $H_2SO_4$ | 0.15-0.25 |
| 1.17 | R1 = R2 = $C_4H_9$ | $H_2O_2$ (30-70%) | 1.0-1.2 | 2-ethylhexanoic acid | 10-25 | $H_2SO_4$ | 0.15-0.25 |
| 1.18 | R1 = C6H4-X; X = halogen, H, $C_1$-$C_5$ alkyl, $C_1$-$C_5$ alkoxy, OH; R2 = $C_1$-$C_5$ alkyl, aryl | $H_2O_2$ (30-70%) | 1.0-1.2 | $C_7$-$C_{10}$[a] | 10-25 | Sulfonic/ sulfuric acid[b] | 0.15-0.25 |
| 1.19 | R1 = 4-MeO-C6H4-; R2 = $CH_3$ | $H_2O_2$ (30-70%) | 1.0-1.2 | Isononanoic acid | 15-20 | $H_2SO_4$ | 0.15-0.25 |
| 1.20 | R1 = C6H4-X; X = halogen, H, $C_1$-$C_5$ alkyl, $C_1$-$C_5$ alkoxy, OH; R2 = $C_1$-$C_5$ alkyl, aryl | $H_2O_2$ (30-70%) | 1.0-1.2 | $C_7$-$C_{10}$[a] | 10-25 | Sulfonic/ sulfuric acid[b] | 0.15-0.25 |

-continued

| Organic sulfone having a structure of formula I | Peroxide used (% by weight) | Amount (equiv based on sulfoxide) | Carboxylic acid used | Concentration sulfoxide in solvent[a] (weight-%) | Additional Acid used | Amount (equiv based on sulfide/sulfoxide) |
|---|---|---|---|---|---|---|
| 1.21 R1 = (phenyl with X substituent) X = halogen, H, $C_1$-$C_5$ alkyl, $C_1$-$C_5$ alkoxy, OH R2 = $C_1$-$C_5$ alkyl, aryl | $H_2O_2$ (70%) | 1.0-1.5 | $C_7$-$C_{10}$[a] | 10-25 | Sulfonic/sulfuric acid[b] | 0.1-0.3 |
| 1.22 R1 = (phenyl with X substituent) X = halogen, H, $C_1$-$C_5$ alkyl, $C_1$-$C_5$ alkoxy, OH R2 = $C_1$-$C_5$ alkyl, aryl | $H_2O_2$ (70%) | 1.0-1.2 | $C_7$-$C_{10}$[a] | 10-25 | Sulfonic/sulfuric acid[b] | 0.001-0.1 |
| 1.23 R1 = (4-methylbenzyl, CH2-phenyl-CH3) R2 = C1 bis C5 alkyl | $H_2O_2$ (70%) | 1.0-2.0 | 2-ethylhexanoic acid | 10-25 | $H_2SO_4$ | 0.15-0.2 |
| 1.24 R1 = (4-methylbenzyl) R2 = $CH_3$ | $H_2O_2$ (50%) | 1.0-1.2 | 2-ethylhexanoic acid | 15-20 | $H_2SO_4$ | 0.2 |
| 1.25 R1 = (4-methylbenzyl) R2 = $CH_3$ | $H_2O_2$ (70%) | 1.0-1.2 | 2-ethylhexanoic acid | 10-25 | $H_2SO_4$ | 0.001-0.05 |

[a] n-heptanoic acid, n-octanoic acid, 2-ethylhexanoic acid, 2-propylpentanoic acid, neodecanoic acid or isononanoic acid or a mixture of two or more thereof
[b] Sulfonic acid or sulfuric acid or a mixture thereof
[c] Methanesulfonic acid
[d] at 80° C.

Generally, what the choice of suitable measures, modes or means for carrying out the process disclosed herein is concerned, the person skilled in the art will let himself be guided by his general knowledge in the art as well as practical considerations. Generally, what specific process parameters such as equipment, the application or operation thereof, for instance vessel, condenser, mixing devices, such as stirrer e.g. crescent stirrer, disk turbine, impeller stirrer, filter, phase separator, pump, distillation column, is concerned, these are either known to the person skilled in the art or are accessible to him by his general knowledge in the art. While typically equipment for carrying out the oxidation reaction disclosed herein, is fitted with special anticorrosion lining such as enamel or corrosion resistant steel ordinary equipment material may be sufficient otherwise.

The process disclosed herein can be carried out as a batch process, a semi continuous or a continuous process. The process disclosed herein can be carried out at atmospheric pressure or under vacuum or a pressure higher than atmospheric pressure. It may be preferred to perform the reaction at atmospheric pressure or below. It may be most preferred to carry out the reaction at a pressure lower than atmospheric pressure. While it may not be necessary to carry out the process under inert gas atmosphere, it is possible to use an inert gas such as nitrogen during the process or part of the process. It may be possible to use the inert gas, such as nitrogen to strip off water during the process or part of the process. Likewise, the inert gas may be air or a mixture of air and nitrogen. With a view of shortening reaction times, it may be preferred to carry out the reaction under a stream of at least one inert gas, preferably one inert gas, such as nitrogen. Said gas stream may be continuous or intermittently employed. A continuous gas stream after the addition of the peroxide may be preferred.

While a higher or lower gas rate may be possible, a gas rate of from 5 to 120 Nl/h/kg may be preferred. It may be more preferred to use a gas rate of from 10 to 100 Nl/h/kg, such as 20 to 50 Nl/h/kg. Thereby the gas rate in Nl/h/kg can be determined according to DIN 1343, January 1990 as relative gas flow. Much lower gas rates may not lead to reduced reaction times. Much higher gas rates may for economic reasons require that the gas is recycled which in turn leads to more expenditure in process equipment. Carrying out the process under a pressure below atmospheric pressure and a stream of at least one inert gas may result in reaction times which are most favourable. It may be most preferred to carry out the reaction under a pressure of from 100 to 900 mbar, and a gas rate of from 5 to 120 Nl/h/kg, whereby it may be more preferred to use a pressure of from 300 to 800 mbar and a gas rate of from 5 to 100 Nl/h/kg, such as 5 to 50 Nl/h/kg. It may be most preferred to carry out the process using 2-ethylhexanoic acid or isononoic acid or a mixture thereof, an aqueous solution of $H_2O_2$ of from 50 to 70% by weight at 300 to 800 mbar and a gas rate of from 20 to 50 Nl/h/kg.

Carrying out the process under a stream of at least one inert gas or under a stream of inert gas and reduced pressure may result in a destillate comprising water and the at least one carboxylic acid, whereby one carboxylic acid, in particular a branched carboxylic acid, specifically 2-ethylhexanoic acid or isononanoic acid may be preferred. Generally, the concentration of water in the destillate is higher than the concentration of acid. Since the destillate phase separates, it may be preferred to recycle the at least one carboxylic acid so obtained from the destillate. Phase separation may occur spontaneously. Typically, a workup of the at least one carboxylic acid is not needed prior to reusing it as solvent. Whereby one carboxylic acid, in particular a branched carboxylic acid, more particular 2-ethyihexanoic acid or isononanoic acid may be preferred. It is however also possible that the destillate contains no or essentially no or only a very small concentration of the at least one carboxylic acid whereby one carboxylic acid, in particular a branched carboxylic acid, more particular 2-ethylhexanoic acid or isononanoic acid may be preferred. In these cases reusing the destillate can be dispensed with.

What the order, the mode or the means of addition of the reactants or any other compound present in the process disclosed herein is concerned there do not exist specific restrictions. Thus, any addition can be continuous or intermittent. Likewise, the order of addition or mixture of the reactants or any other compound present in the process disclosed herein is not specifically restricted. It may be advantageous to at least partially dissolve the sulfoxide in the at least one carboxylic acid and if present in the additional acid and then add the at least one peroxide at reaction temperature. It may be more preferred to completely dissolve or essentially completely dissolve the sulfoxide in the at least one carboxylic acid. It may be most preferred to add the at least one peroxide in such amounts that the at least one peroxide is essentially consumed prior to the addition of further amounts of the at least one peroxide. It may be further preferred that prior to the addition of the at least one peroxide, the at least one additional inorganic or organic acid is added to the mixture or solution of the sulfoxide in the at least one carboxylic acid.

Generally, the temperature at which the reaction is carried out, is chosen to ensure that the sulfoxide is at least partially dissolved in the at least one carboxylic acid and that the reaction is sustained in an economic fashion. Furthermore, the person skilled in the art appreciates that the temperature may vary in the course of the reaction and that more than one temperature is applied, as well as that the temperature will depend on the reactivity and the sensitivity of the educt, the product, the at least one peroxide as well as the at least one carboxylic acid. Thus, the temperature at which the reaction is carried out may for instance range of from 40 to 100° C., preferably of from 50 to 90° C., most preferred of from 60 to 90° C. in the course of the entire process. Typically, the sulfoxide is at least partially dissolved in the at least one carboxylic acid at a temperature in the range of from 60 to 100° C., preferably of from 70 to 90° C. In most cases, the temperature during the addition of the at least one peroxide may range of from 80 to 90° C., preferably of from 80 to 85° C. Furthermore, typically the temperature is decreased after a desired conversion of the educt is reached, e.g. when the oxidation is completed or essentially completed. While it may be possible to decrease the temperature to a temperature above room temperature such as 30 to 50° C. or below room temperature such as 20° C., 10° C., 0° C. or below, in general the temperature is decreased to a range of from 20 to 40° C.

The organic sulfone obtained by the oxidation may be soluble in the reaction mixture. It may however also partially or entirely precipitate during the oxidation. Generally, an organic sulfone which has a melting point of at least 100° C., in particular at least 120° C. has a tendency to precipitate during the oxidation. It may be preferred that the organic sulfone which precipitated during the oxidation is at least partially redissolved. Generally, it is redissolved in the reaction mixture when a desired percentage of conversion of sulfoxide to organic sulfone is reached, for instance a conversion of 70% by weight or higher. It may be preferred that the conversion is 90% by weight or higher. It may be advantageous to increase the temperature prior to decreasing it. Typically, the organic sulfone, which is precipitated during the oxidation may be redissolved by increasing the temperature of the reaction mixture. Thereby, the general considerations pertain to temperatures to be chosen as discussed above apply. In most cases, temperatures to redissolve the organic sulfone range of from 90 to 110° C., preferably of from 95 to 100° C. Generally, the redissolved organic sulfone precipitates again upon decreasing the temperature below 50° C., in particular to 40° C. or below, whereby it may be necessary to decrease the temperature to below room temperature such as to 10° C.

Generally, the so treated organic sulfone has a higher purity compared to organic sulfone, which precipitated during oxidation and is not redissolved. In addition, typically the peroxide is essentially entirely or entirely destroyed. In particular, the peroxide, such as $H_2O_2$, is destroyed to such an extent that workup can be carried out without the addition of quenching agents.

The reaction mixture may comprise water, e.g. by addition of aqueous solutions of for instance the at least one peroxide, or since in case of use of hydrogen peroxide, water is generated in the course of the oxidation reaction. In the process disclosed herein, it may be preferred that water is removed during the oxidation. In particular, water is removed after complete addition of peroxide, while however it is also possible to remove water during the addition of peroxide. It may be preferred that in case of use of hydrogen peroxide, water is removed after a certain conversion of sulfoxide is reached, e.g. at least 50% or higher, in particular 70% or more. Generally, thereby the reaction is facilitated and a faster and more complete conversion ensured. Typically, the water is removed by distillation out of the reaction mixture. Thereby using a pressure below atmospheric pressure and/or a stream of inert gas may support the removal of the water.

While in principle the organic sulfone obtained by the process disclosed herein could be used directly as obtained by the oxidation, that is to say without further workup, typically the organic sulfone is separated from the other components of the reaction mixture. An organic sulfone, which precipitates from the reaction mixture, is generally conveniently collected by filtration. Filtration may therefore be most preferred. Nonetheless, other means of separation from the mother liquor are in principle possible such as centrifugation or draining or any combination of different separation methods such as filtration and draining. Suitable means and conditions for the filtration are either generally known to the person skilled in the art or are accessible to him by making use of what is generally known in the art. For example, it may be possible to use filter press, vacuum filter, centrifugal filter or gravity filter.

After the organic sulfone is separated, it may be subjected to purification methods, such as further distillation, washing or crystallization. It is most preferred that organic sulfone which is collected by filtration is washed with at least one washing solvent, such as one or more washing solvents which dissolves any remains of the reaction mixture and which itself is easily removed from the solid product. It may be preferred to use one washing solvent. It may also be possible to use more than one washing solvent in different washing operations. It may be particularly preferred that the at least one carboxylic acid easily dissolves in the at least one washing solvent used for washing. Possible solvents may be cyclohexane, toluene, methyl tert-butylether, ethyl acetate or acetone or a mixture of two or more thereof. It may be most preferred to use cyclohexane, in particular in case 2-ethylhexanoic acid or isononanoic acid is used alone or in mixture or in mixture with other carboxylic acids, more preferably as the only carboxylic acid during the oxidation.

It may be even more preferred to contact the organic sulfone with at least one washing solvent that comprises water, whereby it may be most preferred to contact it with at least one aqueous base. Thereby the mode of contact is not restricted. The organic sulfone may for instance be washed with or stirred in the at least one washing solvent comprising at least one aqueous base. It may be preferred to wash the organic sulfone with the washing solvent comprising an aqueous base. It may be preferred to use one washing solvent that comprises at least one aqueous base. It may be most preferred to use one aqueous base as washing solvent. It is possible to use the at least one washing solvent that comprises at least one aqueous base in addition to the above washing solvent or washing solvents. In particular, it may be advantageous to remove traces of any of the above acids, in particular 2-ethylhexanoic acid or isononanoic acid by using at least one aqueous base in addition to or as sole washing solvent. It may be possible—and with respect to environmental regards—preferred to dispense with any other washing solvent if at least one aqueous base is employed. It may be particularly preferred to remove traces of strong acid, such as strong inorganic acid, in particular sulfuric acid together with 2-ethylhexanoic acid or isononanoic acid. The at least one, preferably one aqueous base may be a solution of at least one base in water. Thereby it may be preferred that it is a solution of one base in water. The at least one base may be an organic or an inorganic base, whereby the inorganic base may typically be preferred. The at least one base may be a hydroxide, such as an alkali hydroxide, for instance sodium hydroxide or potassium hydroxide or it may be ammonium hydroxide. The base may also be a carbonate, such as alkali carbonate, for instance sodium carbonate or potassium carbonate or a bicarbonate, such as an alkali bicarbonate, for instance sodium bicarbonate or potassium bicarbonate or an ammonia solution. It may be most preferred to use a solution of sodium hydroxide in water.

The concentration of the at least one aqueous base may depend on the substances to be removed from the organic sulfoxide as well as the nature of the organic sulfoxide. Typically, the concentration of the at least one base may be in the range of from 1 to 20% by weight, based on the washing solvent. It may be preferred that it ranges of from 1 to 10% by weight, based on the washing solvent. It may be most preferred that the at least one washing solvent is an aqueous solution of sodium hydroxide in a range of from 2 to 5% by weight, based on the washing solvent, in water.

Generally, it is possible to use water in addition to any other washing solvent. For instance, water may be used to remove traces of a washing solvent comprising an aqueous base. It may therefore be preferred to contact, for instance wash or stir the organic sulfone with water after it was contacted with at least one washing solvent comprising an aqueous base.

It may be advantageous to carry out the washing until the residual amount of substances foreign to the organic sulfone has decreased to an acceptable level. This may depend on the substance in question and may be 1% by weight based on the organic sulfone or less or even to the extent that is no longer detectable. For removing solvent traces or water from the filtration and washing procedure, the organic sulfone can for instance be dried so that the remains of solvent decreases below 2000 ppm, whereby it may be preferred that it decreases below 100 ppm or is reduced to below the detection level.

It may be possible to discard the charged washing solvent. It may however be preferred to most conveniently recycle the at least one carboxylic acid contained in the charged washing solvent by making use of its miscibility gap with water. The at least one carboxylic acid may be contained in the charged washing solvent in form of a carboxylic salt. The latter may be most preferably an alkali carboxylate. Thus, it may generally be preferred to carry out a phase separation between water and the at least one carboxylic acid contained in the charged washing solvent. Phase separation may occur spontaneously. It may be preferred that the phase separation is induced. Induction of phase separation can preferably be achieved by neutralization. It may be preferred that one carboxylic acid, particularly a branched carboxylic acid, specifically 2-ethylhexanoic acid or isononanoic acid comprising sulfoxide, sulfone and the additional stron inorganic acid is recycled from the charged washing solvent. Prior to reusing it, it is possible to workup the at least one carboxylic acid. Using the at least one carboxylic acid without workup may be preferred. It may be more preferred to reuse one carboxylic acid, in particular a branched carboxylic acid, more preferably 2-ethylhexanoic acid or isononanoic acid without further workup after phase separation.

After the separation of the organic sulfone, it may be possible to discard the at least one carboxylic acid or to discard a mixture thereof with at least one other component of the reaction mixture, e.g. discard the mother liquor. The at least one other component may for instance be unreacted educt or norganic acid or a mixture thereof. It is however generally preferred to recycle the at least one carboxylic acid or a mixture thereof with at least one other component of the reaction mixture, e.g. the mother liquor. Thereby, it may be more preferred that the at least one carboxylic acid is an aliphatic, branched carboxylic acid, and it may be most preferred 2-ethyihexanoic acid. It may also be preferred that the branched carboxylic acid is isononanoic acid.

It may be particularly preferred that the at least one carboxylic acid, most preferred 2-ethylhexanoic acid or isononanoic acid containing unconverted educt, that is to say residual sulfoxide, is recycled. Thus, the process as disclosed may preferably comprise that at least one carboxylic acid, in particular 2-ethyihexanoic acid or isononanoic acid, containing sulfoxide is recycled. It may even be more preferred that the at least one carboxylic acid, in particular one carboxylic acid, preferably 2-ethyihexanoic acid or isononanoic acid, or a mixture thereof or a mixture thereof with unconverted educt is recycled following a separation e.g. a filtration. Thereby said educt may be residual sulfoxide. It may be most preferred that the process as disclosed herein comprises that the at least one carboxylic acid, preferably one carboxylic acid is recycled following a separation e.g. a filtration and that the at least one carboxylic acid, preferably one carboxylic acid, comprises sulfoxide.

While it is possible to phase separate and/or to workup the mother liquor, this may not be necessary. Rather it may be preferred to reuse the mother liquor as it is. The at least one carboxylic acid, whereby one carboxylic acid may be preferred, more specifically a branched carboxylic acid, in particular 2-ethyihexanoic acid or isononanoic acid obtained from the distillate or the charged washing solvent or both may be combined with the mother liquor for reuse.

The organic sulfone may be used as starting material in any suitable reaction. A suitable reaction includes, but is not limited to, a polymerization reaction. In particular, the organic sulfone may be used for the production of polymers comprising sulfonic groups. The organic sulfone may be used alone or in combination with one or more suitable compounds such as one or more bifunctional nucleophilic compounds. Polymers comprising sulfonic groups may be polyether sulfones, in particular polyarylene ether sulfones.

Polyarylene ether sulfones, which can be prepared using the organic sulfone prepared according to the process disclosed herein, may preferably be made up of recurring units of the general formula (IV)

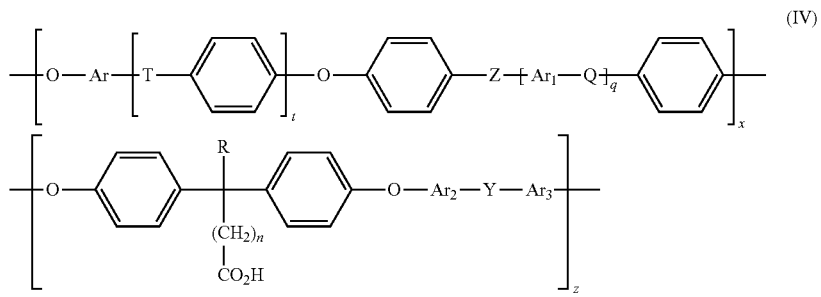

where x is 0.5 or 1, z is 0 or 0.5 t and q are each, independently of one another, 0, 1, 2 or 3,

Q, T, Y and Z are each, independently of one another, a chemical bond or a group selected from among —O—, —S—, —SO$_2$—, S=O, C=O, —N=N—, —R$^c$C=CR$^d$— and —CR$^e$R$^f$—, where R$^c$ and R$^d$ are each, independently of one another, a hydrogen atom or a C$_1$-C$_{12}$-alkyl group and R$^e$ and R$^f$ are each, independently of one another, a hydrogen atom or a C$_1$-C$_{12}$-alkyl, C$_1$-C$_{12}$-alkoxy or C$_6$-C$_{18}$-aryl group, where R$_e$ and R$_f$ are optionally substituted independently by fluorine and/or chlorine atoms or may together with the carbon atom to which they are bound form a C$_3$-C$_{12}$-cycloalkyl group which is optionally substituted by one or more C$_1$-C$_6$-alkyl groups, with the proviso that at least one of the groups T, Q and Z is —SO$_2$— or C=O and, when t and q are each 0, Z is —SO$_2$— or C=O, R is H, C$_1$ to C$_6$ alkyl or —(CH$_2$)n-COOH, wherein n is 1 to 10, Ar, Ar$^1$, Ar$^2$, Ar$^3$ are each, independently of one another, a C$_6$-C$_{18}$-arylene group which is optionally substituted by C$_1$-C$_{12}$-alkyl, C$_6$-C$_{18}$-aryl, C$_1$-C$_{12}$-alkoxy groups or halogen atoms.

It is also possible for different units of the formula (I) to be distributed randomly or in blocks in the poly arylene ether.

Examples of suitable poly arylene ether sulfones are those comprising at least one of the following recurring structural units IV$_1$ to IV$_{29}$ when x=0.5 in formula (IV) and least one of the following recurring structural units IV$_1$ to IV$_{13}$ when x=1 in formula (IV):

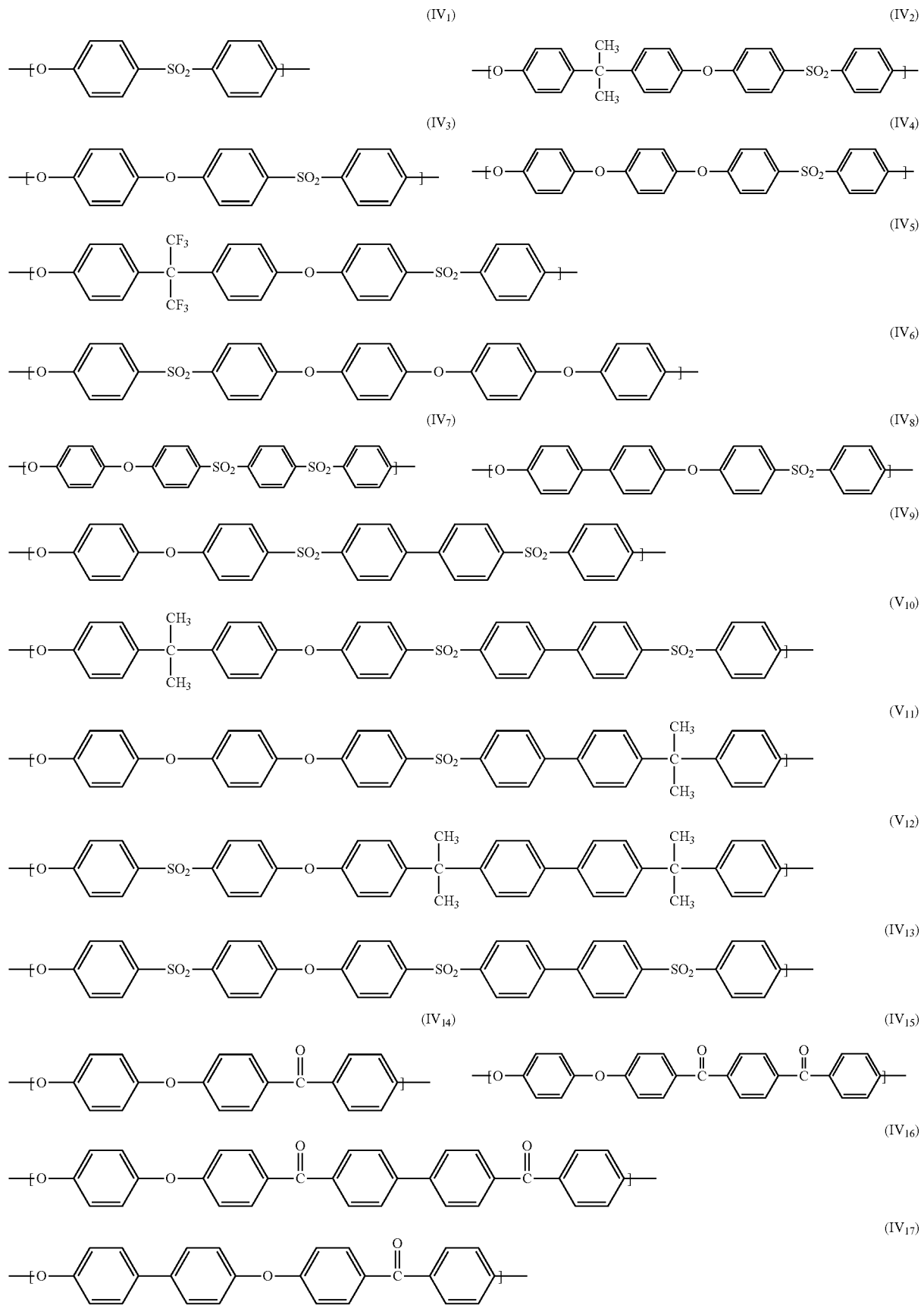

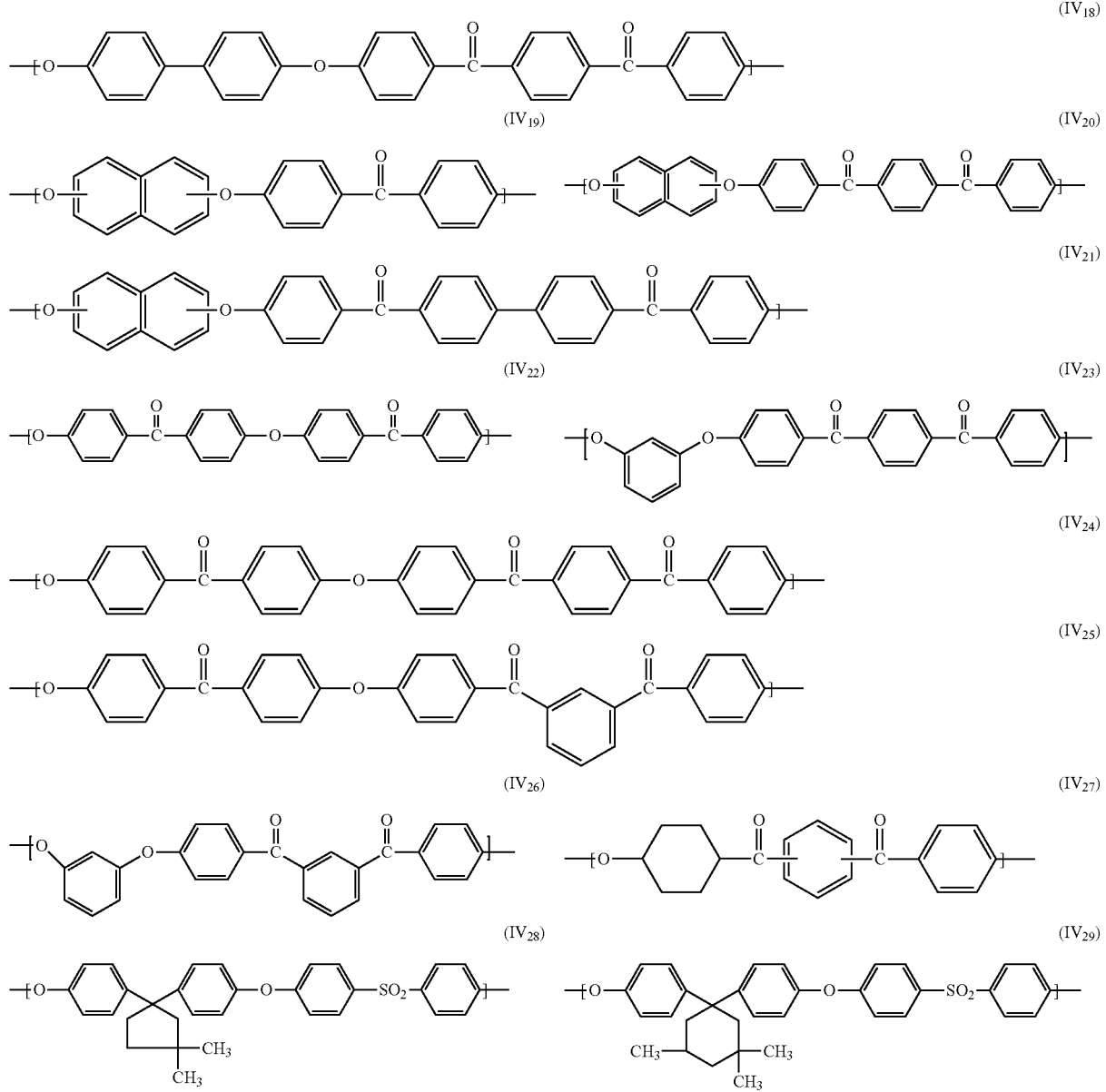

As particularly preferred units of the formula (IV), mention may be made of units of the formula (IV$_1$), (IV$_2$) and (IV$_8$), which can be present either individually or in admixture.

The polyarylene ether sulfones can also be copolymers or block copolymers in which poly arylene ether segments and segments of other thermoplastic polymers, e.g. polyamides, polyesters, aromatic polycarbonates, polyester carbonates, polysiloxanes, polyimides or polyetherimides, are present.

In general, the polymers comprising sulfonic groups may have average molecular weights $M_n$ (number average) of from 500 to 100 000 g/mol, such as of from 1000 to 80 000 g/mol. Poly arylene ether sulfones for instance may have average molecular weights $M_n$ (number average) in the range from 5000 to 60 000 g/mol.

Various processes for the preparation of polymers comprising sulfonic groups are known to the person skilled in the art or are accessible to him by making use of his general knowledge. The polymers obtained from the organic sulfone, which can be prepared using the organic sulfone, prepared according to the process disclosed herein, usually have an improved colour index compared to polymers obtained from organic sulfones prepared according to other processes.

The polymers comprising sulfonic groups and obtained from the organic sulfone prepared according to the process disclosed herein or blends comprising said polymers may be used as molding compositions for producing fibres, films and moldings. There is no specific restriction as to the use of said fibres, films or moldings. A person skilled in the art will appreciate that the polymers comprising sulfonic groups may exhibit special properties such as high temperature resistance, in particular high long term temperature resistance, good bio-compatibility or dimensional stability. Therefore, he will generally use said molding compositions for the production of articles requiring the respective properties. A molding composition comprising polyarylene ether sulfones may for instance be used for the production of household articles, electronic components, laboratory equipment, medical equipment or parts thereof.

The process disclosed herein generally allows for facile recycling of educt and solvent and thus generally for an overall gain in efficiency in use of material and energy. The reaction time using recycled solvent is generally not or not prohibitive longer than using fresh solvent. The process disclosed herein generally allows for a recycling and workup in equipment, which is not restricted to enamel or stainless steel.

EXAMPLES

List of Abbreviations

2-EHA 2-ethyihexanoic acid
DCDPSO 4,4'-dichlorodiphenylsulfoxide
DCDPS 4,4'-dichlorodiphenylsulfone
AcOH glacial acetic acid The solubility of 4,4'-dichlorodiphenylsulfoxide/-sulfone in 2-ethyihexanoic acid at room temperature (22° C.) was determined by formation of a saturated solution of 4,4'-dichlorodiphenylsulfoxide/-sulfone in 2-EHA. A GC spectra was recorded from the liquid phase and the 4,4-dichlorodiphenyl sulfoxide/-sulfone amount determined in area-%.

The nitrogen gas flow is given as relative gas flow in Nl/h/kg according to DIN 1343, January 1990.

Examples 1 and 2: Effect of Peroxide Concentration without Removal of Water 50 g DCDPSO (0.18 mol) were suspended in 250 g of the at least one carboxylic acid (2-EHA) with 20 mol % of an additional acid ($H_2SO_4$ (98%, 0.04 mol)). The mixture was heated to 80° C. and an aqueous solution of $H_2O_2$ was added (see Table I) so that the temperature of the reaction mixture did not increase over 85° C. The addition was completed after 1 h. The mixture was stirred at 80° C. for the time t given below. The entire process was carried out under a nitrogen atmosphere (16 Nl/h/kg). Afterwards, the reaction mixture was heated to 100° C. for 1 h to destroy unconverted $H_2O_2$. During this time, the entire solid dissolved and precipitated after cooling down to 40° C. The solid was filtered off and the mother liquor was separated. The filter cake was washed with cyclohexane. After drying the solid, DCDPS was obtained as white crystalline powder.

TABLE I

| Example | $H_2O_2$ % | $H_2O_2$ equiv. | t h | Yield[a] DCDPS % | Purity DCDPS % |
|---|---|---|---|---|---|
| 1 | 50 | 1.5 | 21.3 | 97 | 98.9 |
| 2 | 70 | 1.2 | 4.3 | 98 | 99.7 |

[a]isolated yield

Examples 3 to 5: Effect of Removal of Water 50 g DCDPSO (0.18 mol) were suspended in 250 g of the at least one carboxylic acid with an additional acid ($H_2SO_4$ (98%, 0.04 mol) as given in Table II below. The mixture was heated to 80° C. and 1.2 equiv. of a 50% by weight aqueous solution of $H_2O_2$ was added so that the temperature of the reaction mixture did not increase above 85° C. The addition was completed after 1 h. The mixture was stirred at 80° C. for the time t given below. During the entire process, water was stripped off with a nitrogen flow of 70 to 160 Nl/h/kg. Afterwards, the reaction mixture was heated to 100° C. for 1 h to destroy unconverted $H_2O_2$. During this time, the entire solid dissolved and precipitated after cooling down to 40° C. The solid was filtered off and the mother liquor was separated. The mother liquor of example 3 was reused for example 8. The filter cake was washed with cyclohexane. After drying the solid, DCDPS was obtained as white crystalline powder.

TABLE II

| Example | Carboxylic acid | $H_2SO_4$ mol % | t h | Yield[a] DCDPS % | Purity DCDPS % |
|---|---|---|---|---|---|
| 3 | 2-EHA | 20 | 3.0 | 94 | 99.5 |
| 4 | Isononanoic acid | 20 | 3.0 | 91 | 99.5 |
| 5 | 2-propylheptanoic acid | 21 | 4.3 | 85 | 98.7 |

[a]isolated yield

Examples 6 and 7: Effect of Removal of Water and Washing Solution 100 g DCDPSO (0.37 mol) were suspended in 500 g of the at least one carboxylic acid (2-EHA) containing $H_2SO_4$ (98%, 0.04 mol). The mixture was heated to 80° C. A stream of nitrogen gas was blown continuously through the reaction mixture with a nitrogen flow given in Table III. Then 1.2 equiv. of a 50% by weight aqueous solution of $H_2O_2$ was added at such a rate that the temperature of the reaction mixture did not increase above 85° C. The addition was completed after 1 h. The mixture was stirred at 80° C. for the time t given below. Afterwards, the reaction mixture was heated to 100° C. for 1 h to destroy unconverted $H_2O_2$. During this time, the entire solid dissolved and precipitated after cooling down to 40° C. The solid was filtered off and the mother liquor was separated. The filter cake was washed with an aqueous solution of sodium hydroxide in water (2.5% by weight) and water. After drying the solid, DCDPS was obtained as white crystalline powder (see Table III).

TABLE III

| Example | Relative gas flow Nl/h/kg | Pressure mbar | t h | Washing Solvent ml | Water ml | Yield[a] DCDPS % | Purity DCDPS % | c[H2O] in distillate % | c[2-EHA] in distillat % |
|---|---|---|---|---|---|---|---|---|---|
| 6 | 40 | 100 | 0.5 | 2 × 85 | 3 × 50 | 89 | 99.8 | 80 | 20 |
| 7 | 250 | 1000 | 0.5 | 2 × 100 | 5 × 100 | 91 | 99.9 | 92 | 8 |

[a]isolated yield

The amount of 2-EHA in the distillate could be isolated by phase separation and reused without any further purification.

Examples 8 and 9: Effect of Recycling of the Solvent

The filtrate of 2-EHA, which contained remainder of unreacted DCDPSO, from example 3 was used as solvent for example 8. The amount of carboxylic acid was adjusted with fresh 2-EHA. The recycled carboxylic acid of example 8, which contained remainder of unreacted DCDPSO, was used in example 9. The amount of carboxylic acid was adjusted with fresh 2-EHA. Otherwise examples 8 and 9 were carried out as example 3. The isolated yields and the time t are given in Table 4.

TABLE IV

| Example | t h | Yield[a] DCDPS % | Purity DCDPS % | Amount of fresh adjusted 2-EHA g | c[H2O] in distillate % | c[2-EHA] in distillat % |
|---|---|---|---|---|---|---|
| 3 | 3.0 | 94 | 99.5 |  | 92 | 8 |
| 8 | 4.2 | 105 | 98.9 | 19.3 | 92 | 8 |
| 9 | 2.2 | 99 | 99.7 | 19.3 | 92 | 8 |
| Overall |  | 99 |  |  |  |  |

[a] isolated yield

Comparative Examples $C_1$ to $C_4$: Effect of Nature of Carboxylic Acid and Recycling of the Solvent Comparative Example C1

100 g DCDPSO (0.37 mol) were suspended in 200 g of the at least one carboxylic acid (AcOH). The mixture was heated to 80° C. under an atmosphere of nitrogen (22 Nl/h/kg). Then 1.2 equiv. of a 50% by weight aqueous solution of $H_2O_2$ was added at such a rate that the temperature of the reaction mixture did not increase above 85° C. The addition was completed after 1.5 h. The mixture was stirred at 80° C. for 0.7 h. Afterwards, the reaction mixture was heated to 100° C. The entire solid dissolved and precipitated after cooling down to room temperature. The solid was filtered off and the mother liquor was reused for comparative example C2. It was observed that the filter cake contained a substantial amount of AcOH. Therefore, the filter cake was washed with 2×175 ml water and 1×150 ml cyclohexane. After drying the solid, DCDPS was obtained as white crystalline powder (89%, purity 99.9%).

Comparative Example C2

100 g DCDPSO (0.37 mol) were suspended in 183 g of the mother liquor, from comparative example C1 and additionally, 27 g of fresh AcOH was added. The mixture was heated to 80° C. under an atmosphere of nitrogen (22 Nl/h/kg). Then 1.2 equiv of a 50% by weight aqueous solution of $H_2O_2$ was added so that the temperature of the reaction mixture did not increase over 85° C. The addition was completed after 1.5 h. The mixture was stirred at 80° C. for 2 h. Due to low conversion of DCDPSO of 79% but full conversion of $H_2O_2$, additional 0.3 equiv of a 50% by weight aqueous solution of $H_2O_2$ were added. The mixture was stirred at 80° C. for 2 h. Afterwards, the reaction mixture was heated to 100° C. The entire solid dissolved and precipitated after cooling down to room temperature. The solid was filtered off. The filter cake was washed with 2×175 ml water and 1×150 ml cyclohexane. After drying the solid, DCDPS was obtained as white crystalline powder (77%, purity 97.31%).

If glacial acetic acid was recycled in this way, the reaction time increased and the yields dropped.

Example C3

100 g DCDPSO (0.37 mol) were suspended in 300 g of the at least one carboxylic acid (AcOH). The mixture was heated to 80° C. and 1.2 equiv of a 50% by weight aqueous solution of $H_2O_2$ was added at 800 mbar so that the temperature of the reaction mixture did not increase over 85° C. The addition was completed after 1.5 h. During the entire process, water was stripped off with a nitrogen flow of 58 Nl/h/kg. The mixture was stirred at 80° C. for 1 h. Afterwards, the reaction mixture was heated to 100° C. The entire solid dissolved and precipitated after cooling down to room temperature. The solid was filtered off and the mother liquor was separated. It was observed that the filter cake contained a substantial amount of AcOH. The filter cake was washed with 2×175 ml water and 1×150 ml cyclohexane. After drying the solid, DCDPS was obtained as white crystalline powder (91%, purity 99.9%).

The concentration of AcOH in the distillate was determined to be 84% whereby the rest was water, 16%. A phase separation was not observed. The mother liquor was reused for comparative example C4.

Comparative Example C4

100 g DCDPSO (0.37 mol) were suspended in 259 g of the mother liquor from comparative example C3. Additionally, 60 g of fresh AcOH were added. The mixture was heated to 80° C. and 1.2 equiv of a 50% by weight aqueous solution of $H_2O_2$ were added so that the temperature of the reaction mixture did not increase over 85° C. The addition was completed after 1 h. During the entire process, water was stripped off with a nitrogen flow of 55 Nl/h/kg. The mixture was stirred at 80° C. for 1 h. Afterwards, the reaction mixture was heated to 100° C. The entire solid dissolved and precipitated after cooling down to room temperature. The solid was filtered off. It was observed that the filter cake contained a substantial amount of AcOH. The filter cake was washed with 2×175 ml water and 1×150 ml cyclohexane. After drying the solid, DCDPS was obtained as white crystalline powder (97%, purity 99.8%).

The concentration of AcOH in the destillate was determined to be 82% whereby the rest was water, 18%. A phase separation was not observed.

Example 10: Test of Solubility of Water in Carboxylic Acids

The solubility of water was determined in carboxylic acids at 40° C. The amount was noted:

| Carbonic acid | T (° C.) | c[H2O] |
|---|---|---|
| 2-EHA | 40 | 1.77% by weight (17.7 g/1000 g) |
| Isononanoic acid | 40 | 1.80% by weight (18.0 g/1000 g) |

At higher amounts, separation into two phases was observed.

Gas chromatography (GC):
Column: DB5 60 m×0.32 mm×0.25 μm,
conditions: 100° C.-15K/', 200° C.-10'-5K/250° C.-15K/' 300° C. 5'
Inj. 300° C.
Det. 300° C.
Const. flow 2.4 ml $N_2$/min

The invention claimed is:

1. A process for the preparation of an organic sulfone by oxidation of the respective sulfoxide in the presence of at least one peroxide comprising at least one carboxylic acid which is liquid at 40° C. and has a miscibility gap with water at 40° C. and atmospheric pressure and
wherein the organic sulfone has a structure according to formula (I)

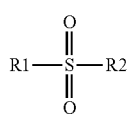

(I)

wherein R1 and R2 are independently from each other
substituted or unsubstituted $C_6$ or $C_{10}$ aryl, wherein the substituents are halogen, hydroxy, cyano, nitro, linear or branched $C_1$ to $C_5$ alkyl, or linear or branched $C_1$ to $C_5$ alkoxy,
linear or branched, substituted or unsubstituted $C_1$ to $C_{20}$ alkyl, wherein the substituents are halogen, tertiary hydroxy, cyano, nitro, substituted or unsubstituted $C_6$ to $C_{10}$ aryl, $C_2$ to $C_{10}$ alkenyl, linear or branched $C_1$ to $C_5$ alkoxy, $C_5$ to $C_7$ cycloalkyl or $C_5$ to $C_7$ cycloalkenyl, or
linear or branched, substituted or unsubstituted $C_3$ to $C_{20}$ alkenyl, wherein the substituents are halogen, tertiary hydroxy, cyano, nitro, $C_1$ to $C_5$ alkoxy or linear or branched $C_1$ to $C_{10}$ alkyl.

2. The process as claimed in claim 1 wherein the solubility of water in the at least one carboxylic acid is less than 2% by weight at 40° C., based on the water/carboxylic acid solution and atmospheric pressure.

3. The process as claimed in claim 1, wherein the at least one carboxylic acid is an aliphatic $C_6$ to $C_{10}$ carboxylic acid.

4. The process as claimed in claim 1, wherein the at least one carboxylic acid is 2-ethylhexanoic acid or isononanoic acid.

5. The process as claimed in claim 1, wherein the peroxide is hydrogen peroxide.

6. The process as claimed in claim 1, comprising removal of water during the oxidation.

7. The process as claimed in claim 1, comprising the presence of at least one further acid with a $pK_a$ of less than 3.

8. The process as claimed in claim 1, wherein the organic sulfone has a melting point of at least 40° C.

9. The process as claimed in claim 1, wherein the sulfone is 4,4'-dichlorodiphenylsulfone having a structure according to formula (II)

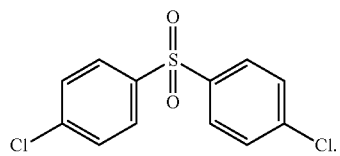

(II)

10. The process as claimed in claim 8, wherein organic sulfone which is precipitated during the oxidation is at least partially re-dissolved in the at least one carboxylic acid.

11. The process as claimed in claim 10, comprising contacting the organic sulfone with at least one aqueous base.

12. The process as claimed in claim 10, wherein the at least one carboxylic acid is recycled.

13. The process as claimed in claim 12 wherein the at least one carboxylic acid contains sulfoxide.

14. The process as claimed in claim 1, wherein R1 and R2 are independently from each other
substituted or unsubstituted $C_6$ or $C_{10}$ aryl, wherein the substituents are halogen, hydroxy, cyano, nitro, linear or branched $C_1$ to $C_5$ alkyl, or linear or branched $C_1$ to $C_5$ alkoxy,
linear or branched, substituted or unsubstituted $C_1$ to $C_{20}$ alkyl, wherein the substituents are tertiary hydroxy, cyano, nitro, substituted or unsubstituted $C_6$ to $C_{10}$ aryl, $C_2$ to $C_{10}$ alkenyl, linear or branched $C_1$ to $C_5$ alkoxy, $C_5$ to $C_7$ cycloalkyl or $C_5$ to $C_7$ cycloalkenyl, or
linear or branched, substituted or unsubstituted $C_3$ to $C_{20}$ alkenyl, wherein the substituents are halogen, tertiary hydroxy, cyano, nitro, $C_1$ to $C_5$ alkoxy or linear or branched $C_1$ to $C_{10}$ alkyl.

15. The process as claimed in claim 1, wherein R1 and R2 are independently from each other substituted or unsubstituted $C_6$ or $C_{10}$ aryl, wherein the substituents are halogen, hydroxy, cyano, nitro, linear or branched $C_1$ to $C_5$ alkyl, or linear or branched $C_1$ to $C_5$ alkoxy.

16. The process as claimed in 3, wherein the at least one aliphatic carboxylic acid is a linear aliphatic $C^6$ to $C^{10}$ carboxylic acid.

17. The process as claimed in 3, wherein the at least one aliphatic carboxylic acid is a linear aliphatic $C^6$ to $C_9$ carboxylic acid.

18. The process as claimed in claim 3, wherein the at least one aliphatic carboxylic acid is n-hexanoic acid or n-heptanoic acid or a mixture thereof.

19. The process as claimed in claim 8, wherein organic sulfone which is precipitated during the oxidation is at least partially re-dissolved in n-hexanoic acid or n-heptanoic acid or a mixture thereof.

* * * * *